US007132105B2

United States Patent
Ruiz Caston et al.

(10) Patent No.: US 7,132,105 B2
(45) Date of Patent: *Nov. 7, 2006

(54) ICOSAHEDRAL SUPERSTRUCTURE OF VP2 OF INFECTIOUS BURSITIS VIRUS (IBDV) AND THE APPLICATION THEREOF

(75) Inventors: Jose Ruiz Caston, Madrid (ES); Jorge Martinez Torrecuadrada, Madrid (ES); Jose Francisco Rodriguez Aguirre, Madrid (ES); Jose Ignacio Casal Alvarez, Madrid (ES); Jose Luis Lopez Carrascosa, Madrid (ES); Narcis Saubi Roca, Madrid (ES)

(73) Assignee: Inmunologia y Genetica Aplicada, S.A., Madrid (ES)

( * ) Notice: Subject to any disclaimer, the term of this patent is extended or adjusted under 35 U.S.C. 154(b) by 64 days.

This patent is subject to a terminal disclaimer.

(21) Appl. No.: 10/483,110

(22) PCT Filed: Jul. 5, 2002

(86) PCT No.: PCT/ES02/00335

§ 371 (c)(1),
(2), (4) Date: Jun. 10, 2004

(87) PCT Pub. No.: WO03/004519

PCT Pub. Date: Jan. 16, 2003

(65) Prior Publication Data

US 2004/0234949 A1    Nov. 25, 2004

(30) Foreign Application Priority Data

Jul. 6, 2001    (ES)    ................................ 200101580

(51) Int. Cl.
*A61K 39/12*    (2006.01)
(52) U.S. Cl. .............................. 424/204.1; 424/207.1; 435/69.1; 435/6
(58) Field of Classification Search ............ 424/204.1, 424/207.1; 435/6, 69.1
See application file for complete search history.

(56) References Cited

U.S. PATENT DOCUMENTS 5,605,792 A    2/1997    Jackwood et al.

OTHER PUBLICATIONS

Caston, Jose R. et al. "C terminus of infectious bursal deisease virus major capsid protein VP2 is involved in definition of the Tnumber for capsid assembly". Nov. 2001. Journal of Virology. vol. 75(22). pp. 10815-10828.
Wang, Min-Ying et al. "Self assembly of the infectious bursal disease virus capsid protein, rVP2, expressed in insect cells and purification of immunogenic chimeric rVP2H particles by immobilized metal-ion affinity chromatography" 2000. Biotechnology and Bioengineering. vol. 67(1). pp. 104-111.
Martinez Torrecuadrada, J. L. et al. "Different architectures in the assembly of infectious bursal disease virus capsid expressed in insect cells". 2000. Virology. vol. 278 (2). pp. 322-331.

*Primary Examiner*—Ali R. Salimi
(74) *Attorney, Agent, or Firm*—Egbert Law Offices (57) ABSTRACT

The IBDV VP2 icosahedral superstructures are made up of 12 empty VP2 dodecahedral capsids, lacking genetic material. They have a size of approximately 60–68 nm in diameter and contain 720 IBDV VP2 subunits. These VP2 icosahedral superstructures can be used for vaccinal and diagnostic purposes.

7 Claims, 6 Drawing Sheets

SEQUENCE LISTING

<160> NUMBER OF SEQ ID NOS: 2

<210> SEQ ID NO 1
<211> LENGTH: 32
<212> TYPE: DNA
<213> ORGANISM: Artificial Sequence
<220> FEATURE:

-continued

```
<223> OTHER INFORMATION: Oligonucleotide primer IBDV1

<400> SEQUENCE: 1
ttcgatgatc acgatgacaa acctgtcaga tc                              32

<210> SEQ ID NO 2
<211> LENGTH: 30
<212> TYPE: DNA
<213> ORGANISM: Artificial Sequence
<220> FEATURE:
<223> OTHER INFORMATION: Oligonucleotide primer IBDV2

<400> SEQUENCE: 2
gagactagat acacagctat cctccttatg                                 30
```

ICOSAHEDRAL SUPERSTRUCTURE OF VP2 OF INFECTIOUS BURSITIS VIRUS (IBDV) AND THE APPLICATION THEREOF

RELATED APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The invention refers to icosahedral superstructures solely constituted of the VP2 protein of the infectious bursal disease virus (IBDV) and to its use for vaccinal and diagnostic purposes.

BACKGROUND OF THE INVENTION

Infectious bursal disease (IBD), or Gumboro Diesease, is an acute course viral disease mainly affecting broiler chickens during the growth stage. This highly contagious disease was first disclosed by Cosgrove in 1962 in the U.S. city of Gumboro (Del.). Currently, this disease is spread worldwide, and the IBD outbreak rate has increased, with a high massive mortality rate (50–75%) caused by highly virulent strains of the virus.

The disease is caused by the infectious bursal disease virus (IBDV), which has a very noticeable tropism of the lymphoid cells located in the bursa of Fabricius, causing a selective elimination of lymphocyte B precursors and, accordingly, the establishment of a severe immunosuppression. Therefore, infection by IBDV causes high massive mortality rates for two reasons: i) the actual infective cycle of IBDV, and ii) opportunistic infections of other pathogens affecting the immunodepressed animals. The immunosuppressive effect of IBDV also reduces the response of the animals to vaccines against other avian pathogens.

The economic importance of this disease is fundamentally based on these two aspects: on one hand, the high mortality rate caused by some IBDV strains in 3-week old chickens, and even older, and on the other hand, the second clinical manifestation of the disease consisting of a prolonged immunosuppression of the birds infected at early ages. The main sequelae associated to said immunosuppression are: dermatitis gangrenosa, anemia-hepatitis syndrome with inclusion bodies, E. coli infections and failures in the efficacy of other vaccinations, such as the vaccinations against the Newcastle disease and infectious bronchitis.

IBDV virions are extraordinarily resistant to environmental conditions and persist in the environment for a period of at least 4 months. The virus is transmitted through water, food or excrement, but there is no vertical transmission through the egg, nor are there chronic carriers of the disease. Therefore, success in controlling Gumboro disease is based on the application of strict hygiene and disinfection programs in the facilities, together with the preventive vaccination of reproducers and progeny. Immunization of reproductive birds has a special importance in the transmission of passive immunity to the progeny; however, the presence of said passive immunity can interfere in the efficacy of the vaccination of the progeny.

IBDV is the prototype of the genus *Avibimavirus* of the Birnaviridae family, a double-stranded RNA (dsRNA) virus. IBDV virions have a size of 60–65 nm, they are not enveloped and have icosahedral symmetry. The viral capsid, formed by a single layer of an average thickness of 9 nm, is constituted of two proteins: VP2 (40 kDa) and VP3 (32 kDa), which are assembled to form a non-spherical T=13 capsid. The genome of the virus is constituted of two double-stranded RNA segments of 3,129 bp (segment A) and 2,759 bp (B), respectively. Segment A contains two Open Reading Frames (ORF) called A1 and A2. ORF A1 encodes a 106 kDa protein with autoproteolytic capability. Processing of the protein gives way to three mature protean products: VP2 and VP3, which form the viral capsids, and VP4, a non-structural protein with proteolytic activity. ORF A2 encodes for a non-structural 16.5 kDa protein (VP5), the activity of which is unknown. Segment B encodes a single, 90 kDa protein, VP 1, with RNA-dependent RNA polymerase activity, which is found in purified virions associated to the ends of both viral genome fragments.

Segment A encodes for a precursor polyprotein in the 5'-VPX-VP4-VP3-3' order. The precursor polyprotein is processed through different proteolytic processes to produce the definitive mature viral proteins, VP2 and VP3, structural components of the IBDV virion, and VP4, the viral protease responsible for processing the precursor polyprotein. It is known that during viral infection, VP2 is initially synthesized as a precursor (VPX), the C-terminus end of which is processed by proteolysis to the mature form during capsid assembly, but the exact cutting points and the proteins involved in said processing are unknown. This processing is essential in the capsid assembly process. VP2 contains the antigenic regions responsible for the induction of neutralizing antibodies, serotype and strain specificity, whereas VP3 is considered the group-specific antigen.

The serological response to the virus is mainly focused on the proteins of the capsid, VP2 and VP3. The VP3 protein is immunodominant, being invariably recognized by sera of convalescent chickens and hyperimmune animals. However, the majority of the monoclonal antibodies capable of neutralizing infectiveness of the virus recognize conformational epitopes in the VP2 protein.

Several vaccines have been disclosed which contain attenuated live IBDV (U.S. Pat. No. 5,632,989), as well as vaccines with inactivated IBDV, as well as recombinant subunit vaccines containing the IBDV VP2 protein, expressed in several systems, for example, bacteria, yeasts, viruses, etc., normally in the form of a fusion protein (U.S. Pat. No. 5,605,792 and U.S. Pat. No. 5,605,827). The possibility that VP2 forms empty chimeric capsids in combination with all or part of IBDV VP3 (U.S. Pat. No. 5,788,970, Hu et al., 1999; Wang et al., 2000; Martínez-Torrecuadrada et al., 2000a; Martínez-Torrecuadrada et al., 2000b; Cheng et al., 2001) is also known.

BRIEF SUMMARY OF THE INVENTION

The invention generally confronts the problem of providing a recombinant subunit vaccine capable of effectively protecting animals against infection caused by IBDV.

The solution provided by this invention is based on the fact that the inventors have identified icosahedral superstructures exclusively constituted of IBDV VP2, which have a high immunogenic power. These superstructures lack genetic material and can be used to effectively and safely protect animals susceptible to being infected by IBDV against the infection caused by said virus, as well as in the direct or indirect diagnosis of IBDV.

The production and characterization of said IBDV VP2 icosahedral superstructures is shown in Example 1, whereas their immunogenic capability to induce protection in chickens against a challenge with a virulent IBDV strain is shown in Examples 2 and 3, which show that the efficacy of a recombinant subunit vaccine comprising said VP2 icosahedral superstructures is equal to or slightly greater than that of a conventional vaccine with inactivated antigen.

A vaccine such as the one provided by this invention has numerous advantages related to safety, as it prevents infective virus handling, and it eliminates the risk that, due to a deficient inactivation of the virus, the virus can again become infective, as well as advantages related to industrial production of said vaccine, since it allows productive process standardization and uniformity of product.

Therefore, an object of this invention is constituted of said IBDV VP2 icosahedral superstructures.

An additional object of this invention is constituted of a recombinant subunit vaccine against infectious bursal disease, comprising said IBDV VP2 icosahedral superstructures.

Another further object of this invention is constituted of the use of said VP2 icosahedral superstructures in the diagnosis of IBDV in a biological sample of an animal susceptible to being infected by IBDV, either by means of reaction with antibodies which recognize IBDV VP2, or by means of the obtainment of antibodies against said IBDV VP2 icosahedral superstructures, and subsequent reaction of said antibodies with IBDV.

BRIEF DESCRIPTION OF THE SEVERAL VIEWS OF THE DRAWINGS

FIG. 1A shows a schematic representation of the IBDV polyprotein NH2-VPX-VP4-VP3-COOH, in which the VPX-VP4 cleavage site, recently suggested in $Ala_{512}$-$Ala_{513}$ (Sánchez & Rodríguez, 1999; Lejal et al., 2000) is shown; the cleavage site for the conversion of VPX into the mature VP2 form is around the 450–456 residues, but is unknown; the VP2 used is shown in the lower part. FIG. 1B shows a photograph of a gel showing VP2 expression by AcVP2.IBDV; purified VP2 was subjected to 11% SDS-PAGE and was detected by staining with Coomassie blue; the purified IBDV particles were subjected to the same treatment and to staining with silver; the bands corresponding to the VP 1, VPX, VP2 and VP3 proteins and the molecular weight markers (kDa) are indicated. FIG. 1C shows a photograph of a gel showing the detection of VP2 particulate material and of IBDV virions by Western blotting with anti-VPX/VP2 polyclonal rabbit serum.

FIG. 3A shows IBDV particles, whereas FIG. 3B shows VP2 capsids, the large VP2 capsids (called VP2 icosahedral superstructures in this description) being identified by means of large white arrows, whereas the black arrows identify small VP2 capsids, showing a snap shot of a VP2 icosahedral superstructures in the moment they were disintegrating in the small box. The length of the bar is 100 nm.

FIG. 4A shows a graph of the refined orientations determined for each particle used for computing the three-dimensional maps; the orientations of each particle are mapped in the icosahedral asymmetric unit (darker region in the icosahedron in the upper right corner), and they are the angles specifying the orientation of the capsid with regard to the direction of the view. FIG. 4B shows a series of images of the VP2 icosahedral superstructures taken directly from the original cryomicrograph (left column) compared with the projected view (right column) of the three-dimensional reconstruction in the corresponding orientation. VP2 icosahedral superstructures selected close to a fivefold (top, designated as 5f), threefold (center, designated as 3f) and twofold (bottom, designated as 2f) axis of symmetry are shown.

FIG. 6A shows a set of three-dimensional representations of the surface of the VP2 icosahedral superstructures seen along a fivefold (top, left), threefold (top, right) and twofold (bottom, left) axis of icosahedral symmetry. A model is shown with the front half of the protein shell sectioned along a fivefold axis (bottom, right). FIG. 6B shows a set of three-dimensional representations of the surface of the small VP2 capsids seen along a fivefold (top) and threefold (intermediate) axis of icosahedral symmetry. Furthermore, a model is shown with the front half of the protein shell sectioned along a threefold axis. FIG. 6C shows three-dimensional representations of the outer (left) and inner (right) surface of the IBDV capsids seen along a threefold axis of icosahedral symmetry. The length of the bar is 100 Å.

DETAILED DESCRIPTION OF THE INVENTION

The invention provides an IBDV VP2 icosahedral superstructure, hereinafter VP2 icosahedral superstructure, or VP2IS, exclusively constituted of IBDV VP2 and made up of 12 empty IBDV VP2 dodecahedral capsids. The VP2 icosahedral superstructure lacks genetic material, it has a size of approximately 60–68 nm in diameter, it contains 720 IBDV VP2 subunits, and has a high antigenic and immunogenic power.

It has surprisingly been observed that when IBDV VP2 (alone) is expressed in insect cells, VP2 dodecahedral capsids are spontaneously formed, which can be assembled to form large icosahedral structures formed by 12 dodecahedral capsids, each dodecahedral capsid being an empty T=1 shell made up of 20 trimeric groups (Example 1). Said large icosahedral structures are those which have been called large VP2 capsids or "VP2 icosahedral superstructures"

(VP21S) in this description, and they can be observed by means of cryoelectron microscopy techniques.

Figure 1:
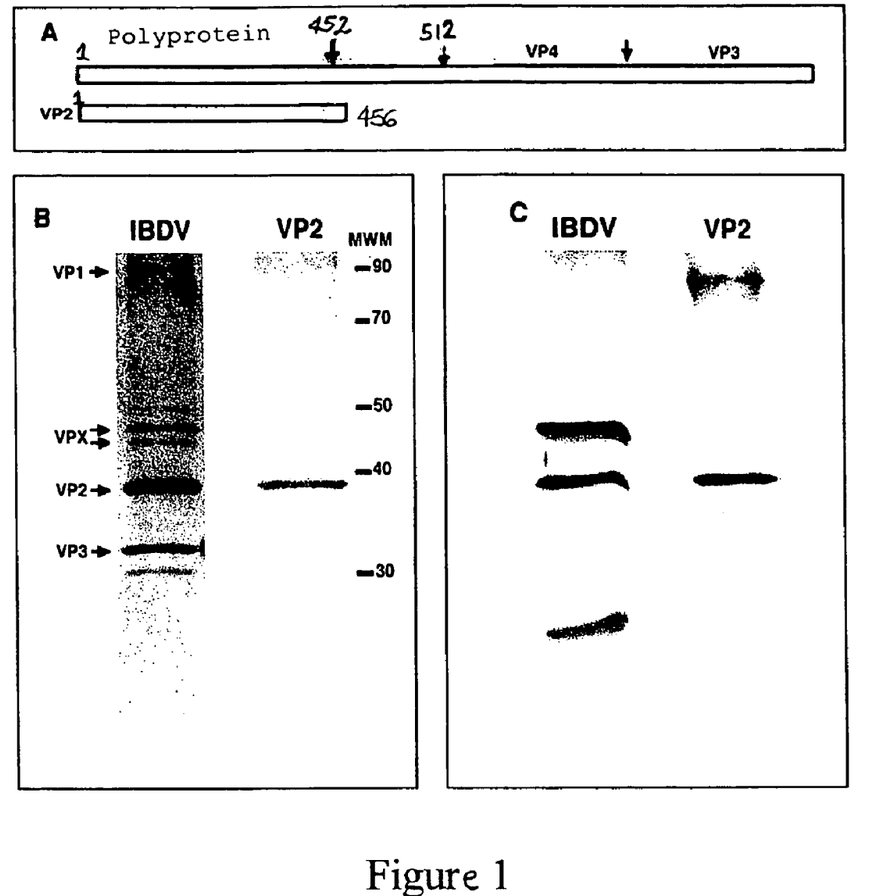
FIG. 1 shows the expression of the VP2 particulate material.

As an illustrative example, the VP2 icosahedral superstructure can be obtained by means of expression in insect cells transformed with a recombinant baculovirus containing the DNA sequence encoding the IBDV VP2 (Example 1.1.2). The VP2 sequence can be obtained and amplified by means of PCR of the IBDV genome using the suitable primers, for example, the primers identified as IBDV 1 (SEQ. ID. NO.: 1) and IBDV2 (SEQ. ID. NO.: 2), which allow amplifying an IBDV genome fragment containing from nucleotide (nt) 1 to 1,368 of ORFA1, and encodes the IBDV VP2. Specific cutting sites for generating compatible ends can be included for subsequent cloning in a suitable vector, for example, in the baculovirus transfer vector pAcYMI. The resulting plasmid (pAcYMI-VP2.IBDV) was used to construct the recombinant baculovirus (AcVP2.IBDV) by means of conventional methods. Said recombinant baculovirus was used to infect Sf9 cells (Example 1.1.3) which were harvested 72 hours post-infection and were processed following a conventional protocol, purifying the particulate material through a 25% sucrose cushion and a 25–50% linear sucrose gradient, both in PES buffer (25 mM piperazine-N,N'-bis(ethanesulfonic acid) [PIPES], pH 6.2, 150 mM NaCl and 20 mM $CaCl_2$). The particulate material, which contained VP2, was identified by means of SDS-PAGE and Western blotting with anti-VPX/VP2 rabbit serum (FIG. 1), choosing the fractions rich in VP2 particles for carrying out structural studies by means of electron microscopy, cryoelectron microscopy and image analysis.

Staining the SDS-PAGE gels with Coomassie blue clearly showed that the VP2 particulate material, comprising VP2 dodecahedral capsids or structures, was highly purified. The monospecific VP2/VP2 serum specifically recognized the VP2 protein (FIG. 1C).

Figure 2:
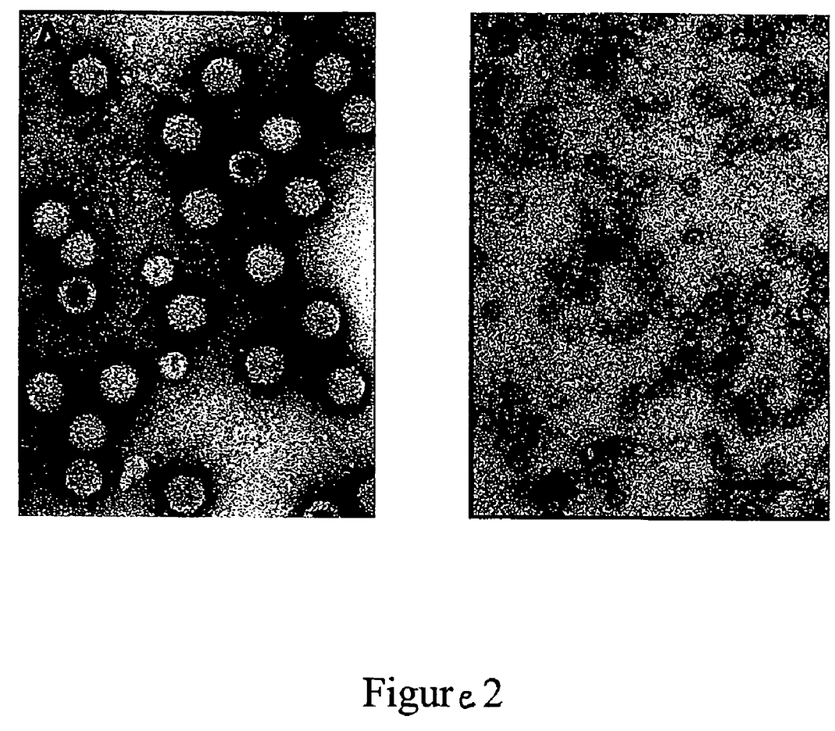
FIG. 2 shows photographs obtained by electron microscopy showing the assembly of VP2 and its comparison with IBDV virions, the purified IBDV virions (FIG. 2A), and donut-like VP2 structures (FIG. 2B) corresponding to the small VP2 capsids being particularly observed. The length of the bar is 100 nm.

Electron microscopy analysis (Example 1.1.4) of the fractions containing said VP2 dodecahedral structures showed that VP2 seems to form a "donut"-like structure of approximately 23 nm in diameter, with a central cavity filled with the negative staining agent (FIG. 2B). These "donut"-like structures have been called "small VP2 capsids" in this description.

Figure 3:
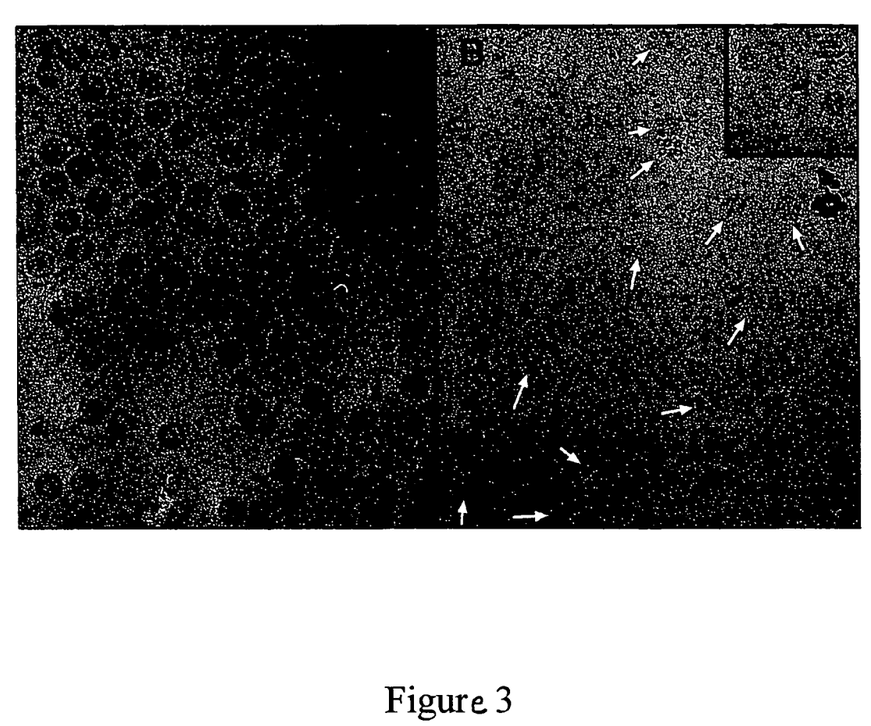
FIG. 3 shows photographs obtained by cryoelectron microscopy showing the assemblies of VP2 and its comparison to IBDV virions.

Upon analyzing the VP2 particles by electron microscopy (Example 1.1.5), not only were small VP2 capsids observed (FIG. 3b, black arrows), but other larger structures, of 55–65 nm in diameter were also observed (FIG. 3B, white arrows), which are formed from said small VP2 capsids ("donut"-shaped dodecahedral structures) since no other protein other than IBDV VP2 was present in the analyzed fractions (FIGS. 1B and 1C). In some cases, snap shots could be taken of said large VP2 structures in the moment they were disintegrating, which were missing one of these smaller constituent elements (FIG. 3B, small box). Said large VP2 structures are those which have been called large VP2 capsids (to differentiate them from the small ones) or "VP2 icosahedral superstructures" in this description.

Figure 4:
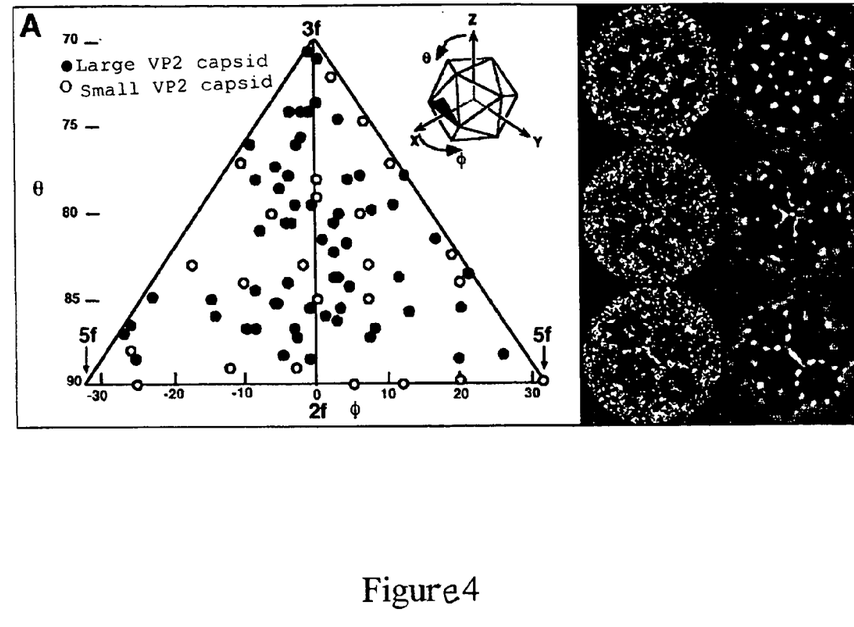
FIG. 4 shows the evaluation of the icosahedral symmetry of the VP2 icosahedral superstructures and the orientations of the small capsids and of the VP2 icosahedral superstructures.
Figure 5:
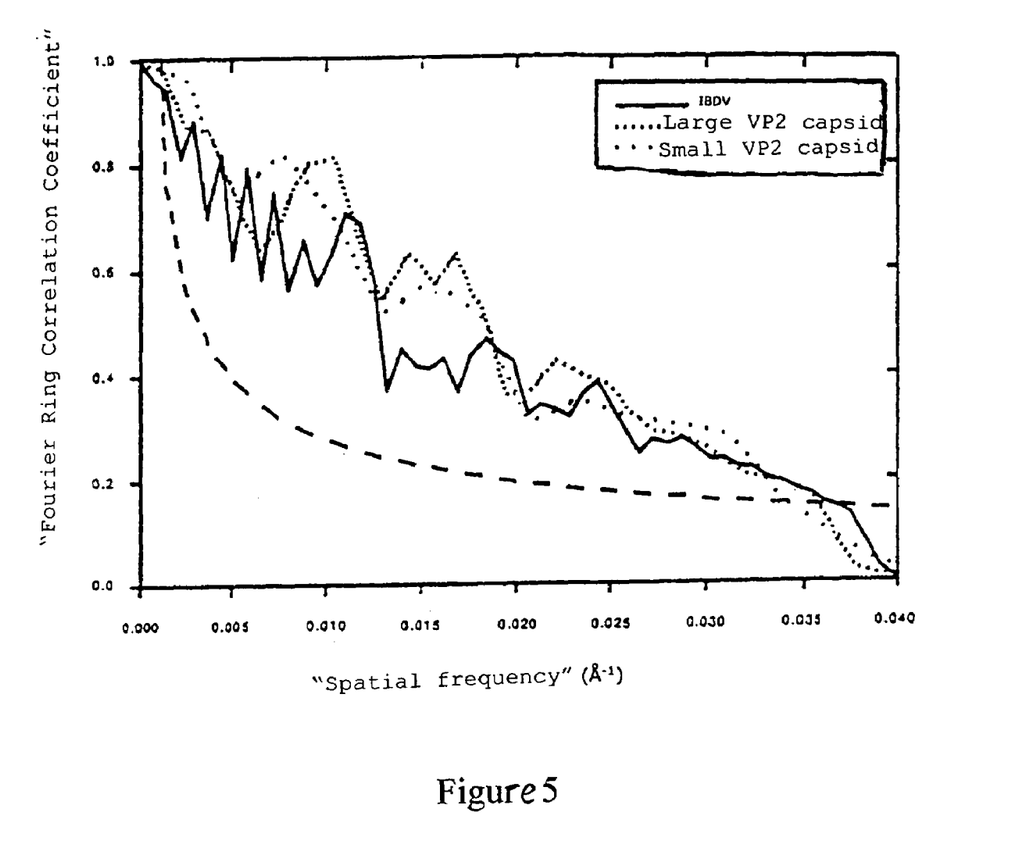
FIG. 5 shows a graph including the evaluation of the resolution by the Fourier ring correlation function for three-dimensional reconstructions of VP2 icosahedral superstructures, small VP2 capsids and IBDV capsids. The resolution limits determined from these graphs are (i) for small VP2 capsids: approximately 29 Å (a spatial frequency of approximately 0.034 Å$^{-1}$), and (ii) for VP2 icosahedral superstructures and for IBDV capsids: approximately 28 Å (a spatial frequency of approximately 0.036 Å$^{-1}$).

The cryoelectron micrograph images of said VP2 icosahedral superstructures (Example 1.1.6) showed a peculiar arrangement of structural units arranged following icosahedral symmetry. The views from the fivefold, threefold and twofold axes of symmetry were relatively abundant and were clearly observed (FIG. 4B, left column). The three-dimensional structure of said VP2 icosahedral superstructure was determined using 72 particles, the orientations of which were uniformly distributed in the icosahedral asymmetric unit (FIG. 4A). To confirm that the orientation of each particle had been correctly determined, the three-dimensional map of the suitable viewing geometry was reprojected and compared with the original images, both visually as well as by means of quantitative criteria, such as the Fourier Ring Correlation method (FIG. 5).

Figure 6:
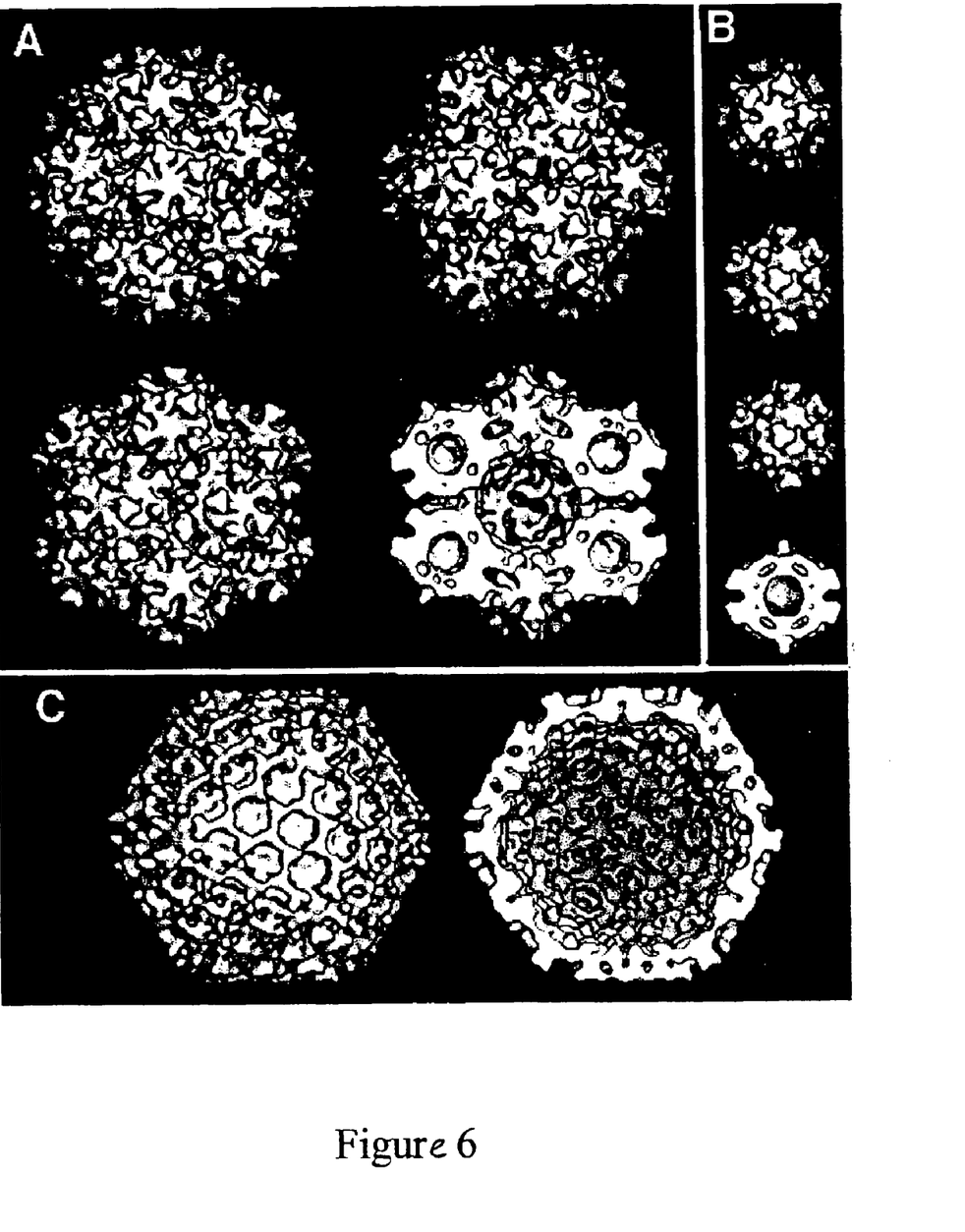
FIG. 6 shows the three-dimensional structure of the VP2 icosahedral superstructures and of the IBDV capsids.

The solid representations of the three-dimensional reconstruction of the VP2 icosahedral superstructure seen from the icosahedral fivefold, threefold and twofold axes of symmetry are shown in FIG. 6A. This model shows 532 symmetry, but it was obtained in the reconstruction process imposing only 522 symmetry. The map was contoured such that continuity of density is observed, although some possible holes may appear filled. The size of the VP2 icosahedral superstructure is approximately 60–68 nm in diameter. This superstructure is an icosahedron formed by 12 smaller dodecahedrons, one in each vertex of the icosahedron, leaving an almost closed internal cavity in the center, as shown in the view with the sectioned front half of the capsid (FIG. 6A, bottom right). The internal cavity is formed by the contribution of one pentagonal face of each dodecahedron. The T=1 dodecahedron is characterized by 20 trimeric projections projecting in the vertices and, because of them, the internal cavity of the VP2 icosahedral superstructure is not occupied by another dodecahedron. The projecting units show a trimeric profile, each trimeric unit contributing to 3 pentagonal faces. As a result, the T=1 capsids (small VP2 capsids) are constituted of 60 VP2 subunits, whereas the VP2 icosahedral superstructures are constituted of 720 VP2 subunits. The five trimeric projections of each dodecahedron oriented towards the internal cavity interact with the other two. It seems that the inside of the small VP2 capsid, as well as the internal cavity of the VP2 icosahedral superstructure, are empty. The essential features of the VP2 icosahedral superstructures, as well as those of the small VP2 capsids, are disclosed in Examples 1.2.3 and 1.2.5, respectively.

The VP2 icosahedral superstructures can be used in the formulation of vaccines for protecting animals against IBDV. Therefore, the invention provides a recombinant subunit vaccine comprising VP2 icosahedral superstructures together with, optionally, an immunologically acceptable diluent and/or adjuvant. The antigen in said vaccines is present in a therapeutically effective amount.

The potency of a vaccine provided by this invention, comprising said VP2 icosahedral superstructures, has been evaluated and compared with a commercially available vaccine (HIPRAGUMBORO BPL-2), which contains inactivated IBDV as an immunogen. The assay was carried out following the European Pharmacopoeia 1997 Guidelines (monograph 1997:0960) with the suitable modifications, and consisted of immunizing different groups of chickens with the different vaccines, by subcutaneous route, and subsequently experimentally infecting the animals with a virulent IBDV strain by oral route (Example 2). The assay included the corresponding infection controls (non-vaccinated but experimentally infected animals) and negative infection controls (neither vaccinated nor experimentally infected animals). Several days prior to immunization and on the same day of immunization, a serological analysis by ELISA and seroneutralization of the animals were carried out to know their condition. Subsequently, different serological analyses were carried out by ELISA on different post-infection days, and the clinical signs of the animals were evaluated. The obtained results showed that:

a) both the group of animals vaccinated with the vaccine provided by the invention and the group of animals vaccinated with the commercial vaccine comply with the minimum requirements of the European Pharmacopoeia: Seroneutralization titer greater than 10,000 Ph. Eu. Units; and that b) both the group of animals vaccinated with the vaccine provided by the invention as well as the group of animals vaccinated with the commercial vaccine withstood the experimental infection very well.

Following a methodology similar to the aforementioned one, an assay was likewise carried out to determine the minimum dose of VP2 icosahedral superstructures of the invention in a vaccinal dose which protects the animals (Example 3). The results obtained in this assay showed that:

a) the animals vaccinated with the vaccine provided by this invention lack clinical signs, or present mild clinical signs, and the isolation of IBDV in the bursa of Fabricius occurs on very few occasions;

b) in the clinical signs, in the post mortem observations and in the isolations, a protection gradient is observed according to the protein dose used, the best results being obtained when 9 µg of VP2 icosahedral superstructures are used, and the poorest results with 1 µg of said superstructures (however, protection of the animals vaccinated with 1 µg of recombinant protein is good); and c) the results of the seroneutralization of the groups of animals vaccinated with 1, 3 and 9 µg of VP2 icosahedral superstructures comply with the requirements of the European Pharmacopoeia.

The invention also provides a method for detecting antibodies recognizing IBDV VP2 in a biological sample of an animal susceptible to being infected by IBDV, which comprises putting said biological sample into contact with VP2 icosahedral superstructures under conditions allowing the formation of an antigen-antibody complex and showing the formation of said complex.

The invention also provides a method for detecting IBDV in a biological sample of an animal susceptible to being infected by IBDV, which comprises putting said biological sample into contact with antibodies recognizing the VP2 icosahedral superstructures under conditions allowing the formation of an antigen-antibody complex and seeing the formation of said complex. The antibodies recognizing the VP2 icosahedral superstructures can be obtained by immunizing animals with said superstructures and separating the antibodies formed. In both cases, seeing the antigen-antibody complex can be carried out by means of the use of conventional techniques known by persons skilled in the art.

The following examples serve to illustrate the invention, and should not be considered limiting of the scope thereof.

EXAMPLE 1

Obtaining IBDV VP2 Superstructures 1.1 Materials and Methods
1.1.1 Preparation of Virus Soroa strain IBDV (Fernández-Arias et al., 1997; Fernández-Arias et al., 1998), a serotype I IBDV strain, was purified by a standard protocol from chicken embryo fibroblasts at an m.o.i. (multiplicity of infection) of 0.1 PFU (plaque forming units) per cell (Fernández-Arias et al., 1998; Lombardo et al., 1999), and was stored in PES buffer at −70° C.

1.1.2 Construction of Recombinant Baculoviruses

The VP2 sequence was obtained by PCR with Vent DNA polymerase (Biolabs), using the pFastBac/POLY recombinant plasmid (Martínez-Torrecuadrada et al., 2000a) as a mold. The oligonucleotides primers used were:

```
IBDV1 [SEQ. ID. NO.: 1]  (5'TTCGATGATCACGATGACAAACCTGTCAGATC3'),
and
IBDV2 [SEQ. ID. NO.: 2]  (5'GAGACTGATCACACAGCTATCCTCCTTATG3'),
``` which cover ORFA1 nucleotides 1 to 1,138 for the amplification of the VP2 encoding gene. The Bc/I sites, which are underlined, have been included for generating the BamHI compatible ends for subsequent cloning in the pAcYMI baculovirus transfer vector (Matsumura et al., 1987). The derived plasmid pAcYMI-VP2-IBDV was sequenced to check its integrity. The corresponding recombinant baculovirus AcVP2.IBDV was obtained according to standard processes (Kitts and Possee, 1993).

1.1.3 Purification of VP2 and VPX Structures

Sf9 cells were infected with AcVP2.IBDV at an m.o.i. of 1 PFU/cell. The cells were harvested 72 hours post-infection (h.p.i.) and were processed following a protocol already described (Martínez-Torrecuadrada et al., 2000a). The particulate material was purified through a 25% sucrose cushion and a 25–50% linear sucrose gradient, both in PES buffer. The particulate material containing the VP2 protein was identified by means of SDS-PAGE and Western blotting with anti-VPX/VP2 rabbit serum (Lombardo et al., 1999; Martínez-Torrecuadrada et al., 2000a). The fractions rich in VP2 were selected for structural studies and were used within 1–2 days after purification.

1.1.4 Conventional Electron Microscopy

5 µl samples were arranged, during 2 minutes, on carbon coated grids. The samples were negatively stained with 2% (w/v) aqueous uranyl acetate. The micrographs were recorded with a Jeol 1200 EXII electron microscope operating at 100 kV at a nominal amplification of ×40,000.

1.1.5 Cryoelectron Microscopy

The fractions containing the virions or structures to be studied by cryoelectron microscopy were collected, centrifuged at 35,000 r.p.m. for 2 hours at 4° C. in an SW 40 (Beckman) rotor, and were resuspended in PES buffer (100–200 µl) at 2–5 mg/ml. Then, they were dialyzed in comparison to PBS buffer (the PES buffer interferes under cryoelectron microscopy analysis conditions), and were diluted until a uniform particle distribution was observed (when they were examined by negative staining). 5 µl drops were applied on one side of a holey carbon film or of a continuous carbon layer on a grid, they were dried by absorption (blot) and the set was submerged in a liquid ethane bath (−180° C.), and the established processes (Dubochet et al., 1988) were followed, essentially as described by Castón et al., (Castón et al., 1997). The micrographs were recorded under minimum exposure conditions, such that the perceived specimens received exposures of 8–10 e−/nm$^2$, at nominal amplifications of ×45,000 or ×40,000 in a Philips CM12 or Jeol 1200 EXII electron microscope, respectively. Gatan 626 cryoholders were used, operating at a temperature of about −171° C. in the two electron microscopes. The microscopes operated at 100 kV and images were recorded with 1 s of exposure on Kodak SO 163 electron image films, which were developed on Kodak D19 at an original concentration for 12 minutes at room temperature. In some experiments, the T4 bacteriophage was vitrified, and the axial spacing of 40.5 Å of its tail sheath was used as an internal amplification standard (Moody & Makowski, 1981). The micrographs were assessed with regard to their resolution and astigmatism by a Fourier analysis by computer and/or optical diffraction analysis, and their defocusing values were estimated from the positions of the first zero of the Contrast Transfer Function (CTF) (Lepault & Leonard, 1985). The first zero of the selected analyzed micrographs was about $(26 \text{ Å})^{-1}$.

1.1.6 Image Analysis

The micrographs were digitalized on an Eikonix IEEE B 488 camera with a square pixel size corresponding to 5.3 (×45,000 negatives) or 6 (×40,000 negatives) Å/pixel. General image processing operations were carried out using a PIC software system (Trus et al., 1996), running on an Alpha DPW 600au (Compaq) work station. The protean particles were removed and pre-processed using the automated process of Conway et al. (Conway et al., 1993). Particle orientations were determined by "common line" processes in the Fourier Transforms (Crowther, 1971; Fuller, 1987; Baker et al., 1988). Model-based processes were used for all subsequent orientation and phase origin refinements (Baker & Cheng, 1996). For reconstruction of the small VP2 capsid, only model-based processes were used, and as a starting model, another small VP2 capsid removed from the large VP2 capsid was used. As an internal control, its three-dimensional structure was calculated without imposing icosahedral symmetry using a weighted back projection method and distributing the orientations along the entire orientation space by randomly selecting equivalent views which were related to the original ones by symmetry (Trus et al., 1996; Radermacher, 1992). The resulting density map was similar to that obtained with the method based on icosahedral symmetry, but at a lower resolution (data not shown).

Reconstructions, with a set of particles suitably representing the icosahedral asymmetric unit, were calculated by using the Fourier-Bessel techniques (Crowther, 1971), and complete icosahedral symmetry (532) was imposed on the final density maps. The underfocus value of the selected electron micrographs allowed reconstructions of the structures to a resolution within the first zero of the Contrast Transfer Function (CTF) of the electron microscope. No corrections due to the CTF were introduced in the reconstruction. Each reconstruction was based on data from several micrographs taken in the same session so as to include in the final model 72 images of "large VP2 particles" (VP2 icosahedral superstructures), 33 images of "small VP2 particles" and 75 images of IBDV. The resolution of the final reconstructions was estimated in approximately 28 Å in terms of spatial frequency at which the Fourier Ring Correlation (FRC) correlation dropped to zero (Saxton and Baumeister, 1982; Conway et al., 1993). Data quality was also assessed by eigenvalue spectra (Fuller et al., 1996). At the resolutions obtained, 99–93% of the mean inverse eigenvalues of the 72, 33 and 75 particles were less than 0.01, indicating that the data were suitably sampled in the Fourier space (Crowther et al., 1970). Reliability of the reconstructions was also tested by back projection of the three-dimensional maps together with the orientations of the individual particles included in the reconstructions.

1.2 Results 1.2.1 Expression and Characterization of IBDV VPX and VP2 Proteins

The baculovirus AcVP2.IBDV contains an insert of 1,368 nt in length expressing a protein with 456 amino acids. The VP2 protein was expressed in insect cells and was purified by means of a sucrose cushion followed by a sucrose gradient. Fractions containing this protein were concentrated and characterized by SDS-PAGE, Western blot analysis and electron microscopy. Staining the SDS-PAGE gels with Coomassie blue showed that the VP2 particulate material was well purified and was formed by a 41 kDa protein (FIG. 1B). The monospecific VPX/VP2 serum specifically recognized this protein (FIG. 1C). A sample of purified IBDV particles was analyzed (FIGS. 1B and 1C, respectively) as a control.

Analysis by electron microscopy of these fractions containing the particulate material showed that VP2 seems to form a donut-like structure of approximately 23 nm in diameter (small VP2 capsids)(FIG. 2B). All the VP2 capsids showed a central cavity filled with negative staining agent. The IBDV samples were also analyzed and the typical polygonal contour of 65–70 nm in diameter was observed (FIG. 2A).

1.2.2 Cryoelectron Microscopy of the VP2 Particulate Material and IBDV

The main advantage of cryoelectron microscopy over conventional electron microscopy techniques is based on the fact that biological molecules are observed in a frozen hydrated state in amorphous ice which closely resembles the native aqueous state. For this reason, VP2 structures were analyzed by cryoelectron microscopy, other larger structures of 55–65 nm in diameter (FIG. 3B, white arrows) being observed together with the small VP2 capsids (FIG. 3B, black arrows). These larger structures, initially called large VP2 capsids (to distinguish them from the small donut-shaped VP2 capsids) and, subsequently, VP2 icosahedral superstructures (VP2IS), are formed from the small VP2 capsids since no protein other than VP2 was present in the analyzed fractions (FIGS. 1B and 1C). In some cases, snap shots of said “large VP2 capsids” could be taken in the moment they were disintegrating, which lacked one of these smaller constituent elements (FIG. 3B, small box).

In comparison, IBDV capsids were also analyzed by cryoelectron micrograph, observing that they were as described, i.e. approximately 70 m in diameter at their widest point (FIG. 3A), they showed a more polygonal rather than circular contour, and there were visible, evident indented areas around their peripheries. The variations in density within the capsid can reflect different dsRNA packaging degrees.

1.2.3 Structure of the VP2 Icosahedral Superstructures

The cryoelectron micrograph images of the VP2 icosahedral superstructures showed a peculiar arrangement of structural units arranged following icosahedral symmetry. The views according to the fivefold, threefold and twofold symmetries were relatively abundant and were clearly observed (FIG. 4B, left column). The three-dimensional structure of the VP2 icosahedral superstructures was determined using 72 particles, the orientations of which were fairly uniformly distributed in the icosahedral symmetrical unit (FIG. 4A). To confirm that the orientation of each particle had been correctly determined, the three-dimensional map of the suitable viewing geometry was reprojected and was compared with the original images both visually (some examples are shown in FIG. 4B, left and right columns) and by quantitative criteria such as the Fourier Ring Correlation method (FIG. 5).

Surface representations of the three-dimensional reconstruction of the VP2 icosahedral superstructure along the icosahedral fivefold, threefold and twofold axes of symmetry are shown in FIG. 6A. This model shows 532 symmetry, but it was obtained in the reconstruction process imposing only 522 symmetry. The map was contoured such that a continuity of density is observed, although some possible small holes may appear filled. The size of the VP2 icosahedral superstructure ranges from approximately 60 to approximately 68 nm in diameter. This structure is an icosahedron formed by 12 smaller dodecahedrons, one in each vertex of the icosahedron, leaving an almost closed internal cavity in the center, as shown in the view according to the fivefold axis of symmetry, with the central half of the capsid sectioned (FIG. 6A, bottom right). The internal cavity is formed by the contribution of one pentagonal face of each dodecahedron. The T=1 dodecahedron is characterized by 20 structures projecting at the vertices, and because of them the internal cavity of the large VP2 capsid is not occupied. The projecting units, as expected, show a trimeric profile, each trimeric unit contributing to 3 pentagonal faces. As a result, T=1 capsids (small VP2 capsids) are constituted of 60 VP2 subunits and the icosahedral superstructures are constituted of 720 subunits. The five trimeric projections of each dodecahedron oriented towards the internal cavity interact with the other two projections. It seems that the inside of the small VP2 capsid, as well as the internal cavity, are empty.

This assay showed that the overexpression of IBDV VP2 leads to the production of VP2 icosahedral superstructures. This unique arrangement probably reflects a tendency of the VP2 trimers to interact, a feature which can finally lead to the crystalline arrangement of the viral particles found inside the IBDV-infected cells. As far as the inventors know, there are no other examples of high order assembly of viral particles following this geometry.

Since said icosahedral superstructures are formed by the assembly of small IBDV VP2 capsids, and said VP2 contains the antigenic region responsible for the induction of the neutralizing antibodies, the antigenic and/or immunogenic capability of said VP2 icosahedral superstructures was then studied in subsequent assays in order to evaluate their possible use in serological assays rather than using whole virions and, where applicable, to constitute a starting point for the design of subunit recombinant vaccines suitable for preventing infectious bursal disease rather than attenuated live or inactivated IBDV vaccines.

1.2.4 Structure of the IBDV Capsids

For comparative purposes, a three-dimensional reconstruction of the IBDV particles was carried out (FIG. 6B). The IBDV capsid shows the same structural features as those disclosed by Böttcher et al., (Böttcher et al., 1997), although the resolution was limited in this case to 28 Å (FIG. 5). The surface shaded maps were contoured to include a volume which showed the same features as those previously published (Böttcher et al., 1997). The capsid is not isometric and shows a T=13 array, as that disclosed by Böttcher et al., (Böttcher et al., 1997), where 260 units projecting from a continuous shell are trimer clustered. Five different classes of triangular capsomers can be distinguished depending on their different local environment (called a–e). Significant changes can be seen at the selected resolution between the different quasi-equivalent trimers. This fact is reflected in the interactions of each trimer with its neighbors. The e trimers, located on the strictly icosahedral threefold axis, interact fairly closely with their neighbors showing 3 thick arms connecting with surrounding trimers of class d. The c and d trimers, which are enantiomorph forms, show two connecting arms, one thick one and another thinner one. The b trimers also show 3 connecting arms, but only one of them is thick, and the a trimers, located around the strictly icosahedral fivefold axis, had a thick connector arm with b trimers. Following the "mnemonic rule" initially designed for the blue tongue virus (BTV), the a trimers of IBDV would be the P trimers in BTV, b=Q, c=S, d=R and e=T. These connecting arms form an arch-like structure which is located from a radius of approximately 31 nm out to a radius of approximately 35 nm. Under these arches there seems to be small pores in the fine continuous shell, 6 around the local sixfold axis, except in those around the pentamers, where there are 5 pores. The only gaps of density observed between adjacent trimers are between c and d trimers and a and a trimers. In the inner shell, there are only 200 trimeric structures (Y-shaped structures). The 5 expected trimers surrounding each pentamer are replaced by a density forming one rim around another concentric rim. This smaller rim almost closes a pentagonal cavity at the fivefold position. It should be noted that the previously published structure of IBDV (Böttcher et al., 1997) does not show this small density rim. While the vertices of the inner trimers point to the center of the hexamers (local sixfold axis), the outer trimers are rotated approximately 60°, their triangular edges facing the local sixfold and fivefold axes. The outer trimers extend outwards by about 4 nm from the thin shell of approximately 2 nm thick, whereas the inner trimers extend inwardly by approximately 3 nm.

1.2.5 Structure of the Small VP2 Capsids

A dodecahedron was removed from the reconstruction of a VP2 icosahedral superstructure and was used as a model for finding the orientations of the small VP2 capsids, probably produced after the disassembly of the VP2 icosahedral superstructures (FIG. 3B, black arrows). The three-dimensional reconstruction of the small VP2 capsids at a resolution of 29 Å (FIG. 5) showed the same arrangement as the empty T=1 dodecahedron forming the VP2 icosahedral superstructure. The three-dimensional representation of the small VP2 capsid was based on the hypothesis that 60 VP2 molecules form each capsid, and taking a value of 0.73 $cm^3/g$ as the partial specific volume of protein. At this threshold level, the capsid was perforated by 5 small holes of approximately 1.5 nm in diameter around each fivefold position. These trimeric projections were equivalent from the conformational point of view, since they had the same local environment. In comparison to the outer trimeric units of the IBDV capsid, they showed no connecting arm between them, although the size and general topography were essentially identical. The capsid wall was formed by connected densities which were arranged at two different radii: 12 pentagonal platforms around the fivefold axis at an average radius of approximately 9 nm, and 20 smaller islands of density at an average radius of approximately 7 nm, extending inwards on the twofold axis. On the outer surface, the trimeric units projected about 3.5 nm from the pentagonal platform. From this it is possible to predict the general shape of each VP2 monomer. Due to the chirality shown by these T=1 capsids, the right-handed form has been assumed as with the virion particles.

EXAMPLE 2

Evaluation of the Potency of Inactivated Vaccines Prepared with IBDV Subunits

This example was carried out in order to evaluate the immunogenicity of different IBDV recombinant antigens produced in baculovirus when they are used in the formulation of a subunit vaccine.

2.1 Characterization of the Products to Assay

Three recombinant subunit vaccines have been tested against IBDV for comparative purposes. Each one of the vaccines contained a recombinant IBDV protein produced in baculovirus. The three recombinant proteins assayed were the following:
- a) VP2: in form of icosahedral superstructures (VP2IS), obtained according to the process described in Example 1;
- b) VPX: recombinant protein corresponding to the VP2 precursor (amino acids 1–516); this protein was produced and purified according to the protocol described by Martínez-Torrecuadrada et al., 2000a; and
- c) Polyprotein: a mixture of VPX (VP2 precursor), VP3, VP4 and small amounts of VP2; this polyprotein was obtained when expressing the ORF1A of the IBDV genome in the baculovirus system according to the protocol described by Martínez-Torrecuadrada et al., 2000b.

The three vaccines were formulated at 25 µg ratio of protein per vaccinal dose and by using the formulation corresponding to the HIPRAGUMBORO BPL-2 vaccine, adding phosphate buffer saline (PBS) until reaching the dose volume.

The proteins were conserved at 4° C. until the time of preparation of the vaccine, which were conserved at 4° C. until the moment of their use.

2.2 Characterization of the Reference Products

HIPRAGUMBURO BPL-2. Batch ON16. Manufacture date: February 2002. Expiry date: February 2002.

2.3 Characterization of the Strains Used in the Experimental Infection

The IBDV strain used in the experimental infection was IBDV Girona strain (VG-248), a highly virulent strain isolated from animals severely affected by IBDV. This strain is used as a highly virulent reference strain for experimental infection assays in Laboratorios Hipra, S. A. to prove the efficacy of vaccinal preparations.

2.4 Studies with Experiment Animals

50 SPF (specific pathogen free), 4-week old, IBDV seronegative chickens were used. These chickens were distributed into 4 groups of 10 animals (A, B, C and D) and into 2 groups of 5 animals (E and F).

The different vaccine preparations were administered by subcutaneous route at 0.5 ml in a single dose administration. The challenge was administered by oral route at 0.2 ml of viral suspension/chicken.

2.5 Method

TABLE 1

Summary of the design of the experiment

| Group | Antigen | No. animals | Vaccination | vvIBDV infection |
|---|---|---|---|---|
| A | VP2IS | 10 | 0 | 0 |
| B | VPX | 10 | + | + |
| C | Polyprotein | 10 | + | + |
| D | HG-BPL-2 | 10 | + | + |
| E | Inf. Control | 5* | − | + |
| F | Neg. Control | 5* | − | − |

*At the time of experimental infection, non-vaccinated animals are added to groups E and F in order to replace the dropouts. At the time of the infection, group E has 13 animals and group F has 6 animals.

TABLE 2

Chronological calendar of tasks to carry out

| | D − 3 | D0 | D28 | D30 | D31–45 | D45 |
|---|---|---|---|---|---|---|
| Vaccination | | + | | | | |
| Blood Extraction | + | + | + | | + | + |
| Experimental infection | | | | + | | |

The experimental system described in European Pharmacopoeia 1997 (monograph 1997:0960) was used as batch control of the inactivated IBDV vaccines.

2.5.1 Serological Analysis

Assessment of the antibody response against VPX/VP2 was carried out by means of ELISA as described in Martínez-Torrecuadrada et al., 2000a.

To carry out seroneutralization, a W2512 IBDV virus suspension was prepared, containing 100 $TCID_{50}$/0.1 ml. The serological samples were decomplementized at 56° C. for 30 minutes and filtered through a 0.45 µm pore. Twofold serial dilutions of the sera were prepared on a 96-well plate, at 100 µl per well. The virus was added, 100 µl per well, and was left in contact with the corresponding serum for one hour at 37° C. 50 µl of the Vero cell suspension were added and were incubated at 37° C. and 5% $CO_2$ for 7 days. The serum titer is matched with the last dilution capable of neutralizing the 100 $TCID_{50}$ of the virus (the last dilution where a cytopathic effect was not observed).

2.6 Summary of Results and Conclusions

2.6.1 ELISA Results

Table 3 shows the titer of the ELISA (geometric mean of the titer) based on the detection of anti-VPX/VP2 antibodies (Martínez-Torrecuadrada et al., 2000a) in the different animal groups used in this assay.

TABLE 3

Numerical values corresponding to the geometric mean of the ELISA titer from the experimental infection

| Vaccine used | Before vaccination | Before infection | 4 dpi | 7 dpi | 12 dpi |
|---|---|---|---|---|---|
| VP2IS | — | 16634.9 | 17828.9 | 31041.9 | 23525.3 |
| VPX | — | 14481.5 | 7755.9 | 2228.6 | 16254.9 |
| Polyprot | — | 12606.9 | 15520.9 | 20480 | 10240 |
| HG-BPL-2 | — | 10396.8 | 6400 | 5571.5 | 9700.6 |
| No vaccine, infected | — | — | 200 | 336.4 | 2015.9 |
| No vaccine, not infected | — | — | NT | NT | NT |

—: Titer less than 100;
NT: Not tested

A pool of the sera of each group was carried out, and the pool corresponding to D28 extraction was analyzed by ELISA. The results are similar to that of the geometric means (data not shown).

2.6.2 Results of Seroneutralization

A pool of sera from each one of the groups was carried out 28 days after vaccination. The 4 vaccinated groups had a seroneutralization titer exceeding 10,240 (and exceeding 10,000 Eu. Ph. Units, which is the minimum required by the European Pharmacopoeia). In the testing repetition, carrying out higher dilutions, the following results were obtained:

TABLE 4

Results of seroneutralization (SN) of the sera pools of D28 extraction

| Group | SN[1] Titer | Eu. Ph. Units[2] |
|---|---|---|
| A | 102,400–204,800 | 200,000 |
| B | 12,800 | 25,000 |
| C | 51,200–102,400 | 100,000 |
| D | 51,200 | 100,000 |
| E | NEG | — |
| F | NT | — |

[1]Inverse of the dilution of serum neutralizing 100 TCID$_{50}$ IBDV
[2]Minimum required in this test: 10,000 Ph. Eu. Units

2.6.3 Experimental Post-Infection Clinical Signs

Clear clinical signs were only observed in the non-vaccinated animals. In the vaccinated animal groups, a slight despondency was detected only in two animals of group A, a 5 dpi (days post-infection); in one of the animals of group B, at 3 dpi; in one of the animals of group C, at 5 dpi; and in one of the animals of group D, at 4 dpi. The few affected animals and the scarce duration of the symptoms indicate that the animals were protected. No clear relationship between the animals with clinical signs and the lesions in the bursa of Fabricius (BF) observed in the necropsy was observed.

In the animals of the non-vaccinated and infected control group (group E, in which 8 animals were added, 13 animals in total), severe clinical signs and death of the animals were observed: 6 animals died and the rest presented severe clinical signs.

No clinical sign was observed in the animals of group F.

2.6.4 Results of the Necropsy

Muscular lesions: very mild lesions were observed in some of the animals.

Lesions in the BF: very slight hemorrhaging (petechiae) was observed in the majority of the BFs (even in some in group F). The presence of exudate was also observed in some of the BFs. The most affected BFs of the vaccinated groups presented signs of necrosis and more severe hemorrhages. These were especially observed in group B. In the non-vaccinated and infected control group, in the animals that died due to the infection, severe hemorrhages, severe necrosis and edema were observed. In the BFs of the animals that withstood the experimental infection, atrophy of the BF (weight less than 1.5 g), severe necrosis and slight hemorrhaging (petechiae) were observed.

2.6.5 Comparison Between Groups

If the groups are compared according to the number of animals having a certain parameter, the following results are obtained:

TABLE 5

Comparison between groups according to different parameters

| Group | No. animals | No. animals lesion BF > 1 | No. animals BF:BW < 2 | No. animals ELISA < 2000 | SN titer | Mortality |
|---|---|---|---|---|---|---|
| A | 10 | 1 | 1 | 0 | 102,400–204,800 | 0 |
| B | 9 | 5 | 3 | 1 | 12,800 | 0 |
| C | 10 | 3 | 2 | 1 | 51,200–102,400 | 0 |
| D | 10 | 0 | 1 | 1 | 51,200 | 0 |
| E | 13 | 12 | 7 (100% alive) | 13 | NEG | 6 |
| F | 6 | 0 | 0 | 6 | NT | 0 |

These results indicate that the animals of group A, vaccinated with vaccines comprising VP2 icosahedral superstructures, were best protected against experimental infection.

2.7 Conclusions

1. All the vaccines comply with the minimum requirements of the European Pharmacopoeia with regard to protection 2. The animals of group A vaccinated with the VP2 icosahedral superstructures are those which showed better behavior, followed by the animals of groups C (polyprotein) and B (VPX). Therefore, two proteins, VP2IS and Polyprotein, were selected for subsequent studies.

EXAMPLE 3

Study of the Minimum Vaccinal Dose of the IBDV Recombinant Proteins Produced in Baculovirus This study was carried out for the purpose of determining (i) which of the two recombinant proteins selected in Example 2 were optimal for elaborating a recombinant subunit vaccine suitable for protecting animals against IBDV, and (ii) which was the minimum recombinant protein dose in a vaccinal dose protecting the animals.

3.1 Methodology

The features of the experiment designed are included in Tables 6 and 7.

TABLE 6

Summary of the design of the experiment

| Assay group/protein | Group | Number of animals | Amount of protein per vaccinal dose | Vaccine type/route | Experimental infection |
|---|---|---|---|---|---|
| A VP2IS | A.1 | 10 | 9 µg | W/O/SC | YES |
| | A.2 | 10 | 3 µg | W/O/SC | YES |
| | A.3 | 10 | 1 µg | W/O/SC | YES |
| B Polyprotein | B.1 | 10 | 9 µg | W/O/SC | YES |
| | B.2 | 10 | 3 µg | W/O/SC | YES |
| | B.3 | 10 | 1 µg | W/O/SC | YES |
| C/HG-BPL-2 | C | 10 | N.A. | W/O/SC | YES |
| D Control | D.1 | 10 | — | — | YES |
| | D.2 | 4 | — | — | NO |

W/O = Water in oil, inactivated vaccine emulsified with oily adjuvant.
SC: subcutaneous route;
N.A.: Not applicable.

TABLE 7

Outline of the test carried out (D = day)

| | D − 3 | D0 | D28 | D29–D38 | D38 |
|---|---|---|---|---|---|
| Vaccination | | + | | | |
| Experimental infection | | | + | | |
| Sacrifice and necropsy | | | | + | + |

PCR was used in this experiment, in addition to the methodology described in Example 2, in order to detect the presence of IBDV in the BFs of the surviving animals (Majó et al., 2000).

3.2 Results

The results obtained are included in Tables 8, 9, 10, 11 and 12.

TABLE 8

Evaluation of the number of animals presenting mild and severe clinical signs, and death in each one of the groups

| Group | Vaccinal dose | Without clinical signs | Mild clinical signs | Severe clinical signs | Death due to infection |
|---|---|---|---|---|---|
| A.1 | VP2IS 9 µg | 6 | 4 | 0 | 0 |
| A.2 | VP2IS 3 µg | 7 | 3 | 0 | 0 |
| A.3 | VP2IS 1 µg | 5 | 4 | 1 | 0 |
| B.1 | Polyprotein 9 µg | 7 | 0 | 1 | 0 |
| B.2 | Polyprotein 3 µg | 6 | 2 | 2 | 0 |
| B.3 | Polyprotein 1 µg | 3 | 2 | 5 | 0 |
| C | HG-BPL-2 | 2 | 6 | 2 | 0 |
| D.1 | Control no vacc. | 0 | 0 | 2 | 8 |
| D.2 | Control no inf. | 4 | 0 | 0 | 0 |

TABLE 9

Summary of the post-mortem analyses in animals vaccinated with the vaccine comprising VP2 icosahedral superstructures (VP2IS) at different doses

| Group/vaccinal dose | Mortality | BF:BW x1000 Ratio (live animals) | | | | Detection of IBDV in BF by PCR |
|---|---|---|---|---|---|---|
| | | >3 | Between 3 and 2 | Between 2 and 1 | <1 | |
| A.1/9 µg | 0/10 | 10/10 | 0/10 | 0/10 | 0/10 | 0/10 |
| A.2/3 µg | 0/10 | 8/10 | 2/10 | 0/10 | 0/10 | 1/10 |
| A.3/1 µg | 0/10 | 7/10 | 2/10 | 1/10 | 0/10 | 4/9* |

*One sample of a surviving animal of group A.2 was not tested.

TABLE 10

Summary of the post-mortem analyses in animals vaccinated with polyprotein at different doses

| Group/vaccinal dose | Mortality | BF:BW x1000 Ratio (live animals) | | | | Detection of IBDV in BF by PCR |
|---|---|---|---|---|---|---|
| | | >3 | Between 3 and 2 | Between 2 and 1 | <1 | |
| B.1/9 µg | 0/8 | 8/8 | 0/8 | 0/8 | 0/8 | 8/8 |
| B.2/3 µg | 0/10 | 8/10 | 1/10 | 0/10 | 1/10 | 10/10 |
| B.3/1 µg | 0/10 | 8/10 | 1/10 | 1/10 | 0/10 | 10/10 |

TABLE 11

Summary of the post-mortem analyses in vaccinated and non-vaccinated control animals

| Vaccine administered | Group/vaccine Dose | Mortality | BF:BW x1000 Ratio (live animals) | | | | Detection of IBDV in BF by PCR |
|---|---|---|---|---|---|---|---|
| | | | >3 | Between 3 and 2 | Between 2 and 1 | <1 | |
| HG-BPL-2 | C | 0/10 | 10/10 | 0/10 | 0/10 | 0/10 | 1/10 |
| Control inf. | D.1 | 9/10 | 0/1 | 0/1 | 1/1 | 0/1 | 1/1 |
| Control not inf. | D.2 | 0/4 | 2/4 | 2/4 | 0/4 | 0/4 | 0/4 |

TABLE 12

Results of the SN and ELISA against VPX
(geometric means) of the samples at D28

| Group | Vaccinal dose | SN result | Ph. Eu. Units | ELISA VPX (geometric mean) | Detection of IBDV in BF by PCR |
|---|---|---|---|---|---|
| A.1 | VP2IS 9 µg | 1/102,400–1/204,600 | 40,000 | 11762.6 | 0/10 |
| A.2 | VP2IS 3 µg | 1/256,000 | 10,000 | 9554.2 | 1/10 |
| A.3 | VP2IS 1 µg | 1/51,200 | 20,000 | 7760.4 | 4/10 |
| B.1 | Polyprotein 9 µg | 1/51,200 | 20,000 | 3044.3 | 8/8 |
| B.2 | Polyprotein 3 µg | 1/51,200 | 20,000 | 6755.8 | 10/10 |
| B.3 | Polyprotein 1 µg | 1/102,400 | 40,000 | 5120 | 10/10 |
| C | HG-BPL-2 | 1/409,600 | >160,000 | 19108.5 | 1/10 |
| D.1 | — | <1/200 | <76 | 2560 | 1/1 |

3.3 Conclusions

1. Choice of Vaccine Antigen

Clinical signs: the animals vaccinated with VP2 icosahedral superstructures present a complete absence of relevant clinical signs.

Isolation of IBDV in BF: in the animals vaccinated with VP2 icosahedral superstructures, the detection of IBDV by PCR in BF is lower than in the other groups.

Serology: no differences are observed with regard to the number of seropositive animals. The values obtained in the ELISA and SN in the groups vaccinated with the VP2 icosahedral superstructures are higher than those of the polyprotein.

2. Vaccinal dose: In the clinical signs, in the post mortem observations and in the detection of IBDV in BF by PCR, a gradation of protection is observed according to the used protein dose. The best results are obtained with 9 µg of protein, and the worst results are obtained with 1 µg of protein. Nevertheless, protection of the animals vaccinated with 1 µg of protein is good.

3. The SN results of the groups vaccinated with 2, 3 and 9 µg of VP2 icosahedral superstructures or of polyprotein comply with the requirements of the European Pharmacopoeia.

BIBLIOGRAPHY

Baker et al., 1988, Proc. Natl. Acad. Sci. USA, 85:422–426.
Baker & Cheng, 1996, J. Struct. Biol. 116:120–130.
Böttcher et al., 1997, J. Virol. 71:325–330.
Castón et al., 1997, J. Cell boil. 138:975–985.
Conway et al., 1993, J. Struct. Biol. 111:222–223.
Crowther, 1971, Phil. Trans. Roy. Soc. Ser. B, 261: 221–230.
Crowther et al., Prc. Roy. Soc. Lond. A., 317:319–340.
Cheng et al., 2001 Biotechnol. Prog., 17, 318–325.
Dubochet et al., 1988, Q. Rev. Biophys. 21:129–228.
Fernandez-Arias et al., 1997, J. Virol. 71:8014–8018.
Fernandez-Arias et al., 1998, J. Virol. 79:1047–1054.
Fuller, 1987, Cell, 48:923–934.
Fuller et al., J. Struct. Biol. 116:48–55.
Hu et al., 1999, Biotechnology and Bioengineering, 63(6), 721–729.
Kitts & Possee, 1993, BioTechniques, 14:810–817.
Lejal et al., 2000, J. Gen. Virol. 81:983–992.
Lepault & Leonard, 1985, J. Mol. Biol. 182:431–441.
Lombardo et al., 1999, J. Virol. 73:6973–6983.
Majó et al., 2000. Congreso Internacional de Producción y Sanidad Animal (*International Congress on Animal Production and Health*). Expoaviga 2000. Fira de Barcelona (Eds), Barcelona. pp. 161–166.
Martínez-Torrecuadrada et al., 2000a, Clin. Diagn. Lab. Immunol., 7(4):645–651
Martínez-Torrecuadrada et al., 2000b, Virology 278:322–331.
Matsumura et al., 1987, J. Gen. Virol. 68:1233–1250.
Moody & Makowski, 1981, J. Mol. Biol. 150:217–244.
Radermacher, 1992, Electron tomography: Three-dimensional imaging with the transmission electron microscope. J. Frank (ed.), Plenum, New York.
Sánchez & Ródriguez, 1999, Virology, 262:190–199.
Saxton & Baumeister, 1982, J. Microsc. 127:127–138.
Trus et al., 1996, J. Struct. Boil. 116:61–67.
Wang et al., 2000, Biotechnology and Bioengineering, 67(1), 104–111.

DEPOSIT OF MICROORGANISMS

A culture of *Escherichia coli* DH5α cells containing the plasmid pAcYM1-VP2.IBDV was deposited in the Colección Española de Cultivos Tipo (CECT) (Spanish Type Culture Collection), Burjasot, Valencia (Spain), on 6 Jul. 2001, under access number CECT 5953.

We claim:

1. A VP2 icosahedral superstructure of the infectious bursal disease virus (IBDV), comprised of 12 empty IBDV VP2 dodecahedral capsids.

2. A superstructure according to claim 1, lacking genetic material.

3. A superstructure according to claim 1, having a size of approximately 60–68 nm in diameter.

4. A superstructure according to claim 1, further comprising:
    720 IBDV VP2 subunits.

5. A recombinant subunit vaccine comprising:
    IBDV VP2 icosahedral superstructures according to claim 1; and
    a diluent and/or an immunologically acceptable adjuvant.

6. A method for detecting antibodies recognizing the VP2 of the infectious bursal disease virus (IBDV) in a biological sample of an animal susceptible to being infected with IBDV, comprising:
    putting said biological sample into contact with VP2 icosahedral superstructures according to claim 1, under conditions allowing formation of an antigen-antibody complex; and
    detecting formation of said complex.

7. A method for detecting the infectious bursal disease virus (IBDV) in a biological sample of an animal susceptible to being infected with IBDV, comprising:
    putting said biological sample into contact with antibodies recognizing the VP2 icosahedral superstructures according to claim 1, under conditions allowing formation of an antigen-antibody complex; and
    detecting formation of said complex.

* * * * *